(12) United States Patent
Hellinger et al.

(10) Patent No.: US 8,640,053 B2
(45) Date of Patent: Jan. 28, 2014

(54) METHOD AND COMPUTERIZED USER INTERFACE FOR PRESENTATION OF MULTIPLE IMAGE DATA SETS

(75) Inventors: Marion Hellinger, Uttenreuth (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 780 days.

(21) Appl. No.: 12/483,361

(22) Filed: Jun. 12, 2009

(65) Prior Publication Data
US 2009/0313585 A1    Dec. 17, 2009

(30) Foreign Application Priority Data
Jun. 12, 2008    (DE) .......................... 10 2008 028 023

(51) Int. Cl.
*G06F 3/048* (2013.01)
(52) U.S. Cl.
USPC ............ 715/850; 715/848; 715/853; 715/854
(58) Field of Classification Search
USPC .................................. 715/848, 850, 853, 854
See application file for complete search history.

(56) References Cited

U.S. PATENT DOCUMENTS

| | | | | |
|---|---|---|---|---|
| 5,555,354 A * | 9/1996 | Strasnick et al. | ............. | 345/427 |
| 5,835,094 A * | 11/1998 | Ermel et al. | ................... | 715/848 |
| 5,917,488 A * | 6/1999 | Anderson et al. | ............. | 715/838 |
| 6,088,032 A * | 7/2000 | Mackinlay | ..................... | 715/848 |
| 6,243,724 B1 * | 6/2001 | Mander et al. | ................ | 715/273 |
| 6,466,237 B1 * | 10/2002 | Miyao et al. | .................. | 715/838 |
| 6,499,029 B1 * | 12/2002 | Kurapati et al. | .............. | 707/750 |
| 6,505,194 B1 * | 1/2003 | Nikolovska et al. | .......... | 707/768 |
| 6,570,597 B1 * | 5/2003 | Seki et al. | ...................... | 715/835 |
| 7,043,701 B2 * | 5/2006 | Gordon | ......................... | 715/848 |
| 7,065,710 B2 * | 6/2006 | Hayashi et al. | ............... | 715/732 |
| 7,437,005 B2 * | 10/2008 | Drucker et al. | ............... | 382/224 |
| 7,562,312 B2 * | 7/2009 | Rochford et al. | ............. | 715/848 |
| 7,797,641 B2 * | 9/2010 | Karukka et al. | .............. | 715/802 |
| 7,970,240 B1 * | 6/2011 | Chao et al. | ..................... | 382/305 |
| 8,006,185 B2 * | 8/2011 | Marinkovich et al. | ........ | 715/723 |
| 2002/0033848 A1 * | 3/2002 | Sciammarella et al. | ...... | 345/838 |
| 2002/0167546 A1 * | 11/2002 | Kimbell et al. | ............... | 345/790 |
| 2003/0149939 A1 * | 8/2003 | Hubel et al. | ................... | 715/526 |
| 2003/0164827 A1 * | 9/2003 | Gottesman et al. | ........... | 345/419 |
| 2003/0179237 A1 * | 9/2003 | Nelson et al. | ................. | 345/765 |
| 2003/0189602 A1 * | 10/2003 | Dalton et al. | .................. | 345/830 |
| 2004/0150657 A1 * | 8/2004 | Wittenburg et al. | .......... | 345/619 |
| 2004/0193600 A1 * | 9/2004 | Kaasten et al. | .................... | 707/7 |
| 2005/0066292 A1 * | 3/2005 | Harrington | .................... | 715/835 |
| 2005/0091596 A1 * | 4/2005 | Anthony et al. | .............. | 715/712 |
| 2005/0134945 A1 * | 6/2005 | Gallagher | ...................... | 358/527 |
| 2005/0240880 A1 * | 10/2005 | Banks et al. | ................... | 715/836 |
| 2006/0085767 A1 * | 4/2006 | Hinckley et al. | .............. | 715/863 |

(Continued)

*Primary Examiner* — Tuyetlien Tran
(74) *Attorney, Agent, or Firm* — Schiff Hardin LLP

(57) ABSTRACT

In a method and user interface for the presentation of multiple image data sets within the scope of a comparative evaluation, a determination is made of at least three organization parameters that describe a sorting of images within an image data set and/or across image data sets, at least one organization parameter is associated with at least one dimension of a three-dimensional matrix, which one dimension is associated with a spatial direction, the images of the image data sets are arranged in the three-dimensional matrix according to the sorting, using the organization parameters and the dimensions, and at least a portion of the images is shown on a presentation device according to their arrangement in the three-dimensional matrix and the spatial directions.

28 Claims, 5 Drawing Sheets

(56) References Cited

U.S. PATENT DOCUMENTS

| | | | |
|---|---|---|---|
| 2006/0109283 A1* | 5/2006 | Shipman et al. | 345/629 |
| 2006/0161867 A1* | 7/2006 | Drucker et al. | 715/810 |
| 2006/0161868 A1* | 7/2006 | Van Dok et al. | 715/835 |
| 2006/0212833 A1* | 9/2006 | Gallagher et al. | 715/848 |
| 2006/0274060 A1* | 12/2006 | Ni et al. | 345/419 |
| 2007/0070066 A1* | 3/2007 | Bakhash | 345/419 |
| 2007/0124699 A1* | 5/2007 | Michaels | 715/837 |
| 2007/0226652 A1* | 9/2007 | Kikuchi et al. | 715/836 |
| 2007/0230761 A1 | 10/2007 | Gundel et al. | |
| 2008/0065638 A1* | 3/2008 | Brodersen et al. | 707/7 |
| 2008/0066013 A1* | 3/2008 | Brodersen et al. | 715/836 |
| 2008/0307303 A1* | 12/2008 | Louch et al. | 715/273 |
| 2008/0307359 A1* | 12/2008 | Louch et al. | 715/835 |
| 2008/0307360 A1* | 12/2008 | Chaudhri et al. | 715/835 |
| 2009/0007018 A1* | 1/2009 | Ikeda et al. | 715/838 |
| 2009/0019031 A1* | 1/2009 | Krovitz et al. | 707/5 |
| 2009/0158214 A1* | 6/2009 | Arnold et al. | 715/830 |
| 2009/0307623 A1* | 12/2009 | Agarawala et al. | 715/765 |
| 2010/0013757 A1* | 1/2010 | Ogikubo | 345/156 |
| 2010/0162151 A1* | 6/2010 | Class et al. | 715/765 |
| 2010/0220978 A1* | 9/2010 | Ogikubo | 386/95 |

\* cited by examiner

METHOD AND COMPUTERIZED USER INTERFACE FOR PRESENTATION OF MULTIPLE IMAGE DATA SETS

BACKGROUND OF THE INVENTION

1. Field of the Invention

The present invention concerns: a method to present multiple image data sets within the scope of a comparative evaluation, as well as an associated device, and a user interface for the presentation of multiple image data sets within the scope of a comparable evaluation.

2. Description of the Prior Art

With the continuing development of medical image acquisition systems, it is possible to acquire image data sets ever faster, in ever improving quality. In particular, the tomographic modalities of computed tomography (CT), magnetic resonance tomography (MR), positron emission tomography (PET) and single photon emission computer tomography (SPECT) are examples. Ever more and ever larger image data sets thus accumulate that must be assessed. At the same time, a trend exists to examine patients with more than just one modality, and at multiple points in time, so that frequently many image data sets with regard to one patient exist even within the scope of a single finding (diagnosis) or therapy.

This "data flood" must be evaluated quickly and efficiently, often with a comparison of multiple images.

To present image data sets, in particular three-dimensional image data sets, it is known to select a presentation format in which multiple images of the image data set lie atop one another in the manner of a "virtual stack" so that, for example, a physician can review these images in order. It is additionally known for multiple such "virtual stacks" to be shown in parallel. However, such a presentation in which image data sets can be reviewed in parallel in their fixed arrangement is frequently less goal-oriented and intuitive. Time is lost and the evaluation turns out to be more difficult.

SUMMARY OF THE INVENTION

An object of the present invention is to provide a method allowing an intuitive, flexible and goal-oriented presentation of these image data sets in the comparative evaluation of multiple image data sets.

This object is achieved according to the invention are provided in a method for the presentation of multiple image data sets within the scope of a comparative evaluation, which method includes:

determination of at least three organization parameters that describe a sorting of images within an image data set and/or across image data sets, association of at least one organization parameter with at least one dimension of a three-dimensional matrix, which one dimension is associated with a spatial direction, arrangement of the images of the image data sets in the three-dimensional matrix according to the sorting, using the organization parameters and the dimensions, and presentation of at least a portion of the images on a presentation device according to their arrangement in the three-dimensional matrix and the at least one spatial direction.

An intuitive and flexible arrangement of multiple image data sets within the scope of a presentation is achieved in this manner, so that the image data sets can be effectively comparatively evaluated. For this purpose, organization parameters are initially determined that describe a sorting of the images within an image data set or across image data sets. In other words, the organization parameter is a specific sorting criterion which can then be flexibly associated with one of multiple dimensions of a three-dimensional matrix in a second step. Naturally, all organization parameters do not need to be associated with a dimension, but only the organization parameters that are required for the comparative evaluation need be flexibly (in particular according to the desire of the evaluator) or, optionally, automatically associated according to the manner of the evaluation. The images of the image data sets are then sorted in the two-dimensional matrix (which naturally has an appropriate size) corresponding to this assignment, and at least one organization parameter is assigned to every dimension.

Spatial directions at the presentation device are now associated with the dimensions. The sorting within the three-dimensional matrix thus indicates in which order and in which direction the images are ultimately presented on the presentation device. In general, multiple images are advantageously simultaneously presented to facilitate the comparative evaluation.

In an embodiment of the method according to the invention, to select the presented images by navigation within the matrix, a zero-dimensional or one-dimensional input modality can be used for the spatial directions perpendicular to one another, and/or a two-dimensional input modality can be used for two of the spatial directions. In this way an intuitive control is added to the method according to the invention in that an input modality (in particular an input device) is used, that allows a spatial direction to be associated with respective dimensions, and ultimately the matrix can be "scrolled through" in this spatial direction given operation of the input modality. It is advantageous for the presented spatial direction to correspond to the actuation direction of at least a one-dimensional input modality. The method according to the invention is therefore designed more intuitively since a user can associate movements or actuations that he or she makes with the input modality with immediate changes on the presentation device via the presentation of different images.

Given a two-dimensional presentation, two actuation directions of a computer mouse that are input perpendicular to one another by movement on a pad]can be associated with two spatial directions of the two-dimensional presentation, and/or a scroll wheel of the computer mouse can be used to select the presented images in the third dimension. In this example of the use of a computer mouse, three one-dimensional input modalities are thus used in the case of a conventional mouse, or a two-dimensional input modality and a one-dimensional input modality are used in the event of an optical mouse. If the mouse is then moved to the right or left, the following or preceding image (or images) in the first spatial direction is thus shown while another image is no longer shown. A right-left actuation of the mouse therefore also corresponds to a right-left scrolling on the presentation device (in particular a monitor). Forward and back with the mouse are then associated with up and down on the presentation device. The scroll wheel can then serve to scroll through the images of the image data sets that are arranged in the manner of a stack in the third dimension.

In addition to the advantageous use of a computer mouse, other input devices are also conceivable. Examples are a surface input system in which hand movements above a presentation surface are sensed by a sensor device and are translated into input commands. In this case, the input modality is integrated into the presentation device. For example, a table fashioned as a two-dimensional presentation device or a two-dimensional monitor hanging on the wall would be conceivable, with a paging through the images in the corresponding spatial directions enabled by movements of the hand in the spatial directions over the presentation surface. The movement in the third spatial direction can then be enabled by removal from or approach of the hand toward or away from the presentation surface, for example. Such a presentation device connected with a computer, which presentation device has a presentation surface, with an integrated input protocol for the navigation within the matrix, likewise represents a very intuitive input variant.

It should be noted that, in all examples, simultaneous actuation in multiple spatial directions can also naturally be translated so that, for example, a paging through the images in diagonal directions is also enabled.

In addition or as an alternative to the input modality just described for navigation within the matrix, the number of the presented images (and correspondingly their presentation size) can be varied with a zoom function. An additional input element can be used for the zoom function. For example, given use of a computer mouse, the left mouse button can be associated with zooming out, the right mouse button with zooming in. Other embodiments are also conceivable. In this way the evaluator can individually decide which compromise he or she would like to select between size (thus clarity of the presentation) and number of the images that can be simultaneously compared.

With regard to the size of the images, it can additionally be provided that, given a presentation of multiple images, the images are presented in various presentation sizes. In particular, central images can be presented larger than images at the edge. For example, it is possible for a centrally presented image to be shown largest, images surrounding this are shown somewhat smaller and the images at the edge are smallest. For example, if 9 images are simultaneously presented, the central image is shown largest, the four adjoining images are somewhat smaller and the four images situated in the corners are smallest. The central image is thus emphasized. This can in particular be joined very well with the previously described, intuitive input form via the input modalities. Other embodiments are also conceivable, for example two central images shown with the same size, or the like.

In addition to the comparison with images arranged in parallel, or atop and below one another, given a two-dimensional presentation, it can frequently also be desirable to simultaneously enable a comparison of images situated behind one another (thus images arranged in the third dimension or the third spatial direction). For this purpose, in the method according to the invention, given a two-dimensional presentation, a currently shown image is overlapped by a following image and/or preceding image in the third dimension in the matrix, in particular via transparency and/or false color effects. For example, the images lying in the currently shown plane can be formed to be slightly transparent so that the underlying image is recognizable. It is likewise possible to produce an overlapping of the images wherein an image is shown in false colors for differentiation. Both effects can also be advantageously combined with one another.

At the beginning of the method according to the invention, the image data sets can be selected by a user. That means that the user selects the image sets to be evaluated from a database or from a file system.

In addition to a fixed rule and/or the simple citation by a user, for example, there are now multiple additional, advantageous embodiments of the method according to the invention to determine the organization parameters. At least a portion of the organization parameters can be automatically determined from at least one image data set. This means that the criteria, according to which the images present in image data sets can be arranged, are determined using the image data sets to be compared. Essentially two possibilities are possible for this, that can also be cumulatively applied. Organization parameters can be stored in at least one image data set. For example, this is possible in many generally used image data set formats (for example the DICOM format). In addition to the actual image data, image data-describing parameters are stored in this format that, for example, reflect the acquisition modality, acquisition parameters, a contrast agent administration, or the like. It is typical for the image data of an image data set to be positioned relative to one another. This additional information can be read from the selected image data sets, so it can then be provided, for example, that only the organization parameters that are common to all image data sets are retained. Image data set-spanning organization parameters (for example a predetermined arrangement of various modalities) can nevertheless also already be present according to previous determination. As an alternative or in addition to the storage of organization parameters in an image data set, it is also possible to determine at least one organization parameter from the image data of the image data set, in particular by reverse (back) calculation. Acquisition parameters (for example specific sequences or even the modality itself that is used) can typically be determined again from an image data set, wherein evaluation parameters (post-processing parameters) can also simply be back calculated under the circumstances, for example. In this context the image data sets are thus evaluated to the effect that organization parameters or the value of an organization parameter are to be learned from said image data sets.

The organization parameters can be associated with the dimensions by a user. For example, it is possible to generate a neat presentation in which the organization parameters and the spatial directions are presented and then can be linked by the user. For example, a coordinate system can be shown on the display device with axes along which the organization parameters can be dragged by the user via an input device. Dependent on the association (which is in particular controlled by the user), the organization parameters can be represented as icons, for example, that can be selected and then associated with the corresponding spatial direction, for example by dragging the icon onto an axis indicating the spatial direction.

Naturally it is also possible, independent of a user-controlled association, for at least one organization parameter to be represented as an icon in the presentation of the image data sets and/or given the association with a dimension. In any case it is reasonable to also provide an indicator in the presentation of the image data sets according to the present invention, which indicator indicates which organization parameter (thus which sorting criterion) is associated with which spatial direction. Icons are particularly well suited for this.

In another advantageous embodiment of the method according to the invention, it is possible for more than one organization parameter to be associated with a dimension. Then, the sorting of the images in one dimension that is associated with more than one organization parameter ensues in the order of the association of the organization parameters. For example, if the input modality is associated first with one dimension or spatial direction, then at the point in time of acquisition, the images are first organized according to modalities and then according to the acquisition points in time. Naturally (in particular given the user-controlled association of the organization parameters with the dimensions), if icons are dragged onto an axis it is also possible to use the order of these icons as the order of the sorting, for example.

Examples of possible organizational parameters are the acquisition time (in particular with regard to the administration of a contrast agent), and/or the spatial directions within the image data set, and/or at least one image acquisition parameter, in particular a magnetic resonance sequence, and/or at least one evaluation parameter, in particular a filter type; and/or the orientation of the image data set in a patient, and/or the acquisition modality. Naturally, other organization parameters can also be used. In particular, it should be noted that spatial directions within a patient can advantageously also serve as organization parameters. In the method according to the invention, projections or slice images are then determined from the three-dimensional image data sets, even when individual acquired slice images do not lie in the corresponding planes, for example, which projections or slice images are situated in planes perpendicular to the selected spatial direction in the patient (for example caudal-cranial). This means that in this case the image data sets are evaluated so that a sorting using the organization parameters and a corresponding presentation are possible.

Such prepared processing steps for presentation of the images of the image data sets that support the comparative evaluation are conceivable in still greater numbers in the method according to the invention. The images of the image data sets can be registered with one another and/or corrected for distortion before the presentation. Such a registration of the images, which in particular also allows the same regions within a patient to actually be presented, simplifies the comparative evaluation to a large degree. Distortion corrections can also be provided, in particular when images from various modalities in which different distortions occur are compared.

It is likewise advantageously supportive of the comparison when successive images in one dimension of the matrix are shown with the same presentation parameters, in particular when the presentations are adapted to one another with regard to a comparison. Given successive two-dimensional and three-dimensional images in one dimension of the matrix, a two-dimensional projection optimally corresponding to the projection of the two-dimensional image is determined from the three-dimensional images and is presented. A comparison is comfortably enabled in this way without too much information being lost. Moreover, it can be provided that successive images in one dimension can be adapted to one another with regard to the presented anatomical region. For example, corresponding sections can thereby be selected that show exactly the same region, such that a direct comparison is possible. This is particularly useful when superimposed presentations are provided as described.

In addition to the method, the invention encompasses a device for comparative evaluation of multiple image data sets, having a presentation device and at least one input modality, fashioned to implement the method according to the invention. In particular a computer (processor) can be provided for this. Naturally, all advantageous embodiments of the method according to the invention can be implemented in such a device.

Such a device can be particularly advantageously designed when, as already explained in the preceding with regard to the input modality, the input modality is integrated into the presentation device, which in particular has a presentation surface, so the input modality translates movements (for example of a hand) above the presentation surface into a corresponding navigation in the three-dimensional matrix and correspondingly modifies the presentation, thus paging through the images or shifting the displayed section of the three-dimensional matrix.

The invention also encompasses a user interface for presentation of multiple image data sets within the scope of a comparative evaluation, wherein at least three organization parameters that describe a sorting of images within an image data set and/or spanning image data sets can be determined; at least a portion of the organization parameters can be associated with at least one dimension of a three-dimensional matrix that is associated with a spatial direction; the images of the image data set can be arranged in the three-dimensional matrix according to the sorting using the organization parameters and the dimensions; and at least one portion of the images can be presented according to their arrangement in the three-dimensional matrix and the spatial directions.

Like the method according to the invention, the user interface according to the invention also offers an increased flexibility directed toward an optimally goal-oriented evaluation and has functionalities that enable the implementation of the method according to the invention with this user interface. Insofar as they can be applied to a user interface, all embodiments of the method according to the invention are applicable for the user interface.

The user interface can be fashioned for navigation within the matrix based on actuations (operations) of zero- or one-dimensional input modalities respectively associated with the spatial directions perpendicular to one another and/or a two-dimensional input means associated with two of the spatial directions, in particular a computer mouse. The user interface can additionally have a zoom function pertaining of the number of presented images, which zoom function can also in particular be controlled via an input modality.

For a presentation of multiple images, the images can be presented in various presentation sizes; in particular, centrally shown images can be presented larger than images shown at the edges. The size of the images shown on a two-dimensional presentation surface can decrease from the inside to the outside, for example. Additionally or alternatively, given a two-dimensional presentation it can be possible to superimpose a next image and/or a preceding image in the third dimension of the matrix on a currently shown image, in particular by transparency and/or false color effects.

At least one organization parameter can advantageously be represented as an icon in the presentation of the image data sets and/or in the user-controlled association with a dimension.

In order to enable a comparative evaluation in an ideal manner, successive images in one dimension of the matrix can be presented with the same presentation parameters, in particular can be adapted to one another with regard to a comparison. Given successive two-dimensional and three-dimensional images in one dimension of the matrix, a two-dimensional projection optimally corresponding to the projection of the two-dimensional image can be shown from the three-dimensional images. It is additionally possible for successive images in one dimension to be adapted to one another with regard to the presented anatomical region.

DESCRIPTION OF THE PREFERRED EMBODIMENTS

Figure 1:
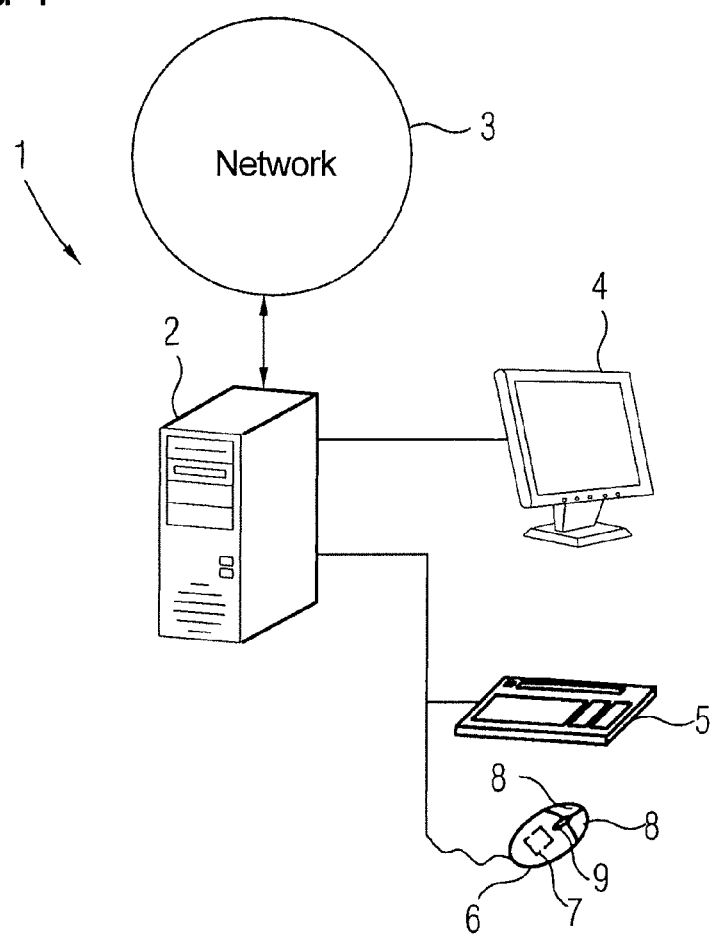
FIG. 1 schematically illustrates the basic components of a device according to the invention.

FIG. 1 shows a device 1 according to the invention having a computer 2 in the memory of which image data sets can be stored. Alternatively or additionally, image data sets can be supplied via a network (schematically indicated with 3) and/or a data medium of the computer 2. For comparative evaluation of multiple image data sets, the device 1 according to the invention also has a two-dimensional presentation device as well as input devices, namely a keyboard 5 and an optical computer mouse 6. The optical computer mouse 6 has a two-dimensional input modality 7 (an optical sensor) to sense movements on a surface, two buttons 8 and a scroll wheel 9. Naturally, a conventional mechanical mouse with a ball can also be used that then has two one-dimensional input modalities that are activated by the ball to sense movements on a surface.

Figure 2:
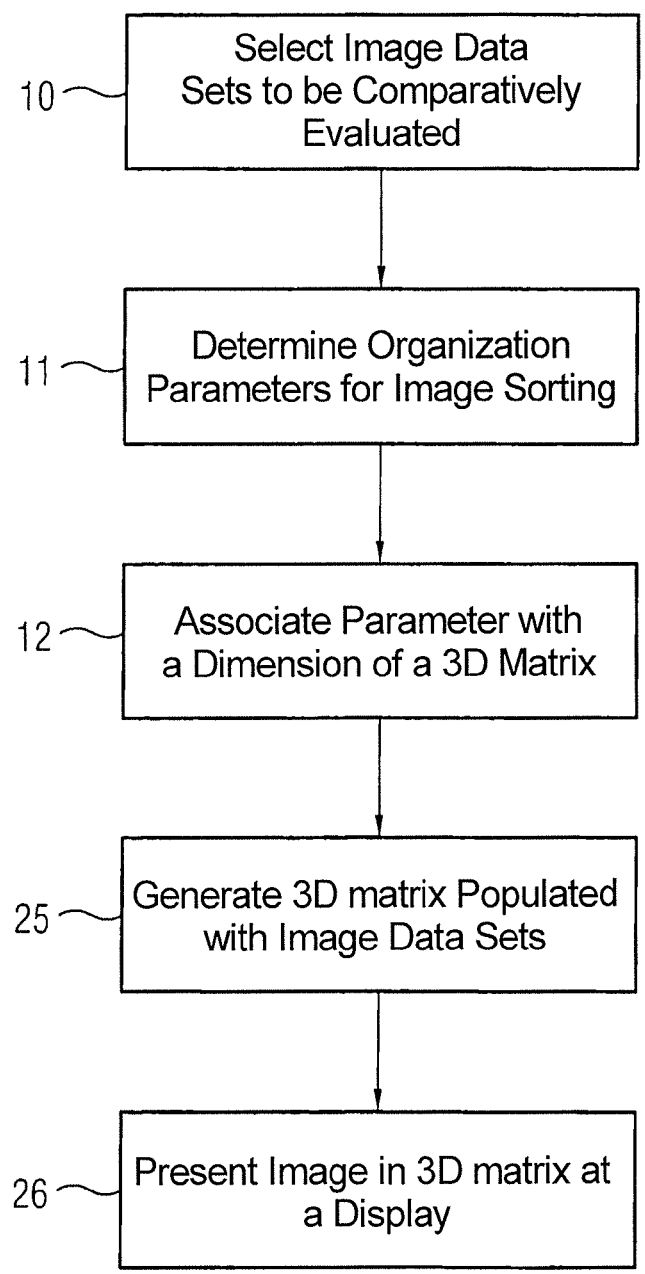
FIG. 2 is a flow chart of an embodiment of the method according to the invention.

The computer 2 is fashioned to implement the method according to the invention, which is explained in detail in the following with reference to FIG. 2.

In Step 10, a user initially selects multiple image data sets that are to be comparatively evaluated. The image data sets can be retrieved from the network 3, from a data medium and/or from a memory of the computer 2, for example. The selected image data sets can originate from different imaging modalities, have been acquired at different points in time, have been acquired with or without contrast agent administration, have been acquired with different acquisition parameters and been post-processed differently, etc. Different criteria according to which the physician would like to sort and compare the images are conceivable for every conceivable comparative evaluation. The method according to the invention offers a flexible and intuitive tool that enables a goal-oriented evaluation.

In Step 11, a number of organization parameters are then determined that describe a sorting of images within an image data set and/or across image data sets. This means that each of the organization parameters is ultimately a sorting criterion according to which the individual images of the image data sets can be arranged. Examples, are at least an acquisition time (in particular relative to the administration of a contrast agent); the spatial directions within the image data set and/or a patient at least one image acquisition parameter, in particular a magnetic resonance sequence; at least one evaluation parameter, in particular a filter type; the orientation of the image data set in a patient; and the acquisition modality. The determination of the organization parameters can ensue in many ways, that may be combined with one another in this exemplary embodiment. It is naturally initially possible for the a user to establish organization parameters. Furthermore, certain organization parameters (for example the acquisition point in time) are already provided in principle for storage on the part of the computer. However, in to the method according to the invention it is in particular possible for at least a portion of the organization parameters to be automatically determined from the image data sets. The image data sets considered here are stored in an extended DICOM format that allows the storage of a number of items of information in addition to the image data, for example: the point in time of acquisition; the acquisition modality; the administration of a contrast agent; diverse acquisition parameters; and post-processing parameters and the like. However, an arrangement of the individual image data points (voxels) relative to one another is contained in each image data set, for example. This is also conceivable as an organization parameter. In addition to the aforementioned possibilities, reference points and reference directions that reflect the position of the image data set in the body of the patient as well as the primary directions dorsal/ventral, cranial/caudal and distal/proximal can also be presented. Some of these parameters represent sorting criteria within the image data set; however others also span across image data sets. For example, whether the acquisition modality is required as an organization parameter can be established in that it is compared whether the image data sets were acquired with different modalities. Organization parameters are also conceivable in which the images of the image data sets are intermixed, for example when this relates to directions relative to the patient. It should be noted that, within the scope of the method, it is also possible (for example) to determine new images from a three-dimensional image data set in orientations that do not correspond to the slices presented during the acquisition. This is discussed again in detail below.

In addition to the determination of organization parameters from information additionally stored in an image data set, organization parameters are also determined (in particular retroactively calculated) from the image data of the image data set. For example, from the data of the image data set it is frequently apparent with which modality these were acquired, even if this information is not additionally stored anyway in the image data set. The retroactive calculation of diverse evaluation parameters is also possible and conceivable in the method according to the invention. The possibility is still provided that information about the position of the image data set in the patient can be deduced via segmentation, for example, in particular with the aid of an anatomical atlas.

Particularly with regard to the steps described in the following, the user interface according to the invention and its functionalities in the interaction with a user and the presentation are also explained in detail simultaneously with the method according to the invention.

Figure 3:
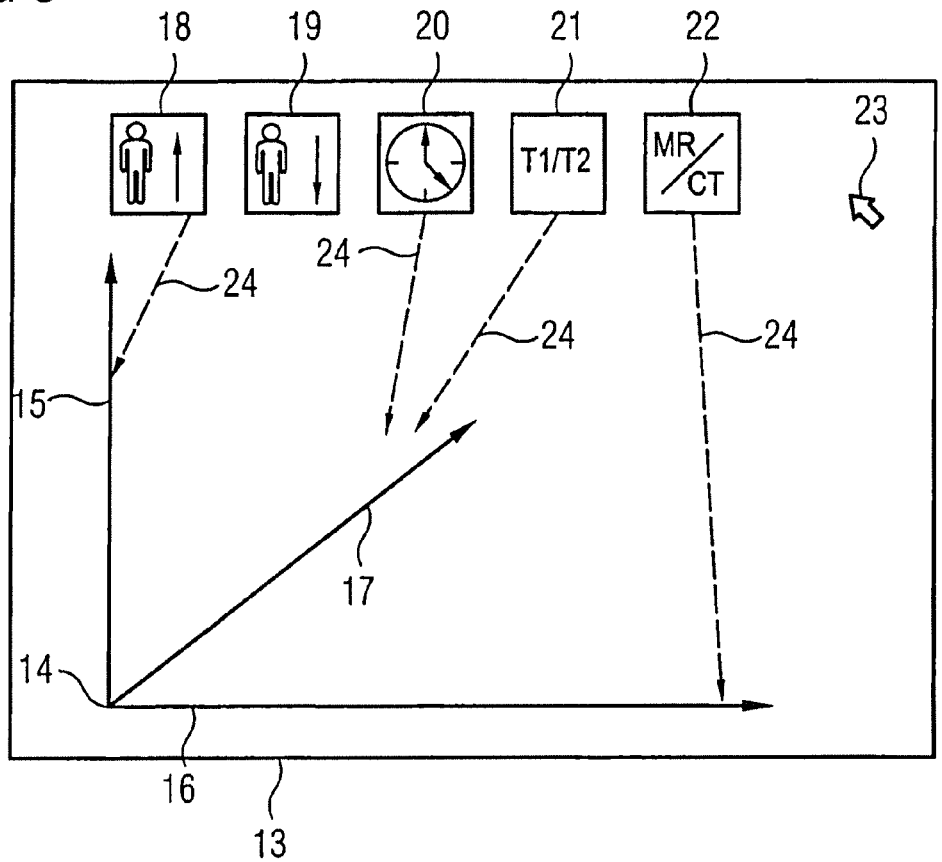
FIG. 3 shows a presentation embodiment for association of organization parameters with dimensions/spatial directions on the user interface according to the invention.

In Step 12, at least one organization parameter is then associated with each of three dimensions of a three-dimensional matrix that are respectively associated with a spatial direction. For example, this can ensue according to fixed organization parameter sets predetermined for specific comparative evaluation types, which organization parameter sets are stored in the computer 2, for example, but in this exemplary embodiment this is conducted by the user. Refer to FIG. 3 for illustration of this procedure. There the user interface 13 according to the invention is shown as it can be displayed (on the presentation device 4, for example) at this stage of the method. Three spatial directions are visible which are associated with dimensions of the three-dimensional matrix, schematically represented by a coordinate system 14. An axis 15, 16, 17 that points in the corresponding spatial direction is thereby associated with each of the spatial directions. Icons 18-22 that symbolize different organization parameters are shown as examples at the top of the screen. These icons can be dragged by the user onto the various axes with the use of the mouse 6 (indicated by a mouse pointer 23). This procedure is shown in detail by the dashed arrows 24 in FIG. 3. By dragging an icon 18-22 onto one of the axes 15-17, the corresponding organization parameter is associated with the corresponding spatial direction. In the present example, the sorting "caudal-cranial" (represented by the icon 18) is associated with the axis 15; the time (represented by the icon 20) and the weighting of the magnetic resonance sequence (represented by the icon 21) are associated with the axis 17; and the modality (represented by the icon 22) is associated with the axis 16.

As shown in the example of the axis 17 (the third dimension or spatial direction) projecting backwards in the screen, multiple organization parameters can also be associated with one dimension or, respectively, spatial direction. The consequences this has are shown in detail in the following.

In Step 25 (FIG. 2 again), a three-dimensional matrix is now generated that is populated with images of the image data sets using the organization parameters and their association with the dimensions. The images of the image data sets are initially sorted according to the sorting criteria that are described by the organization parameters, and then are sorted along the corresponding dimensions (thus spatial directions) in the two-dimensional matrix. If more than one organization parameter is associated with one dimension (as is the case in FIG. 3, for example), the order of the association of the organization parameters is decisive for the sorting order. This means that the example described by FIG. 3 is initially sorted chronologically (which moreover can also ensue in the form of time intervals), afterwards according to T1-weighted or T2-weighted magnetic resonance sequences within the simultaneous images. The new images (already cited) from the image data sets are possibly also calculated in the determination of this matrix if the actual images acquired for the image data set were not situated in the transversal plane given a sorting in the caudal-cranial direction.

Figure 4:
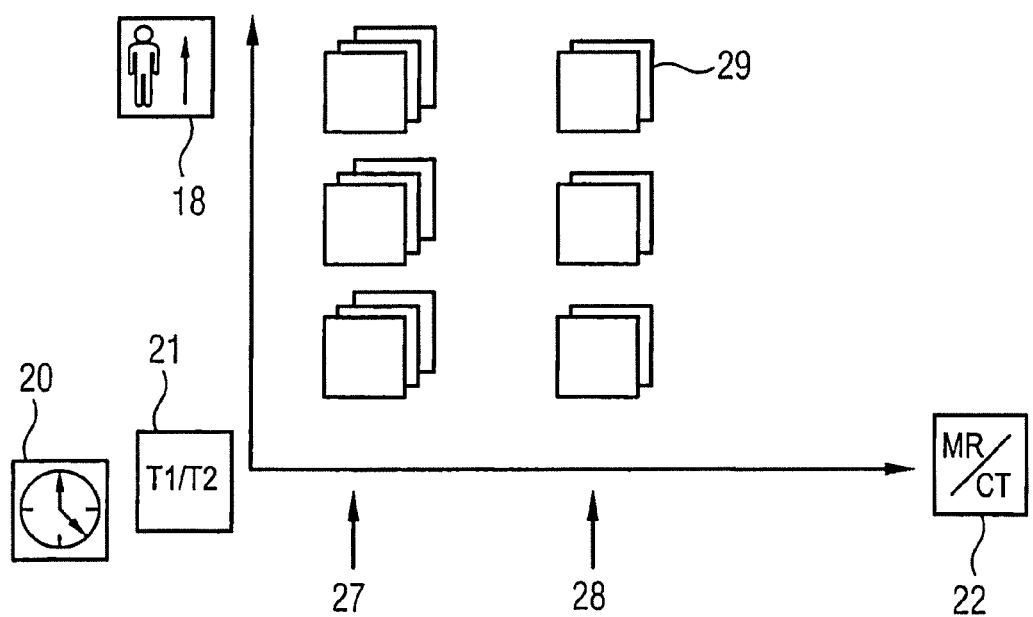
FIG. 4 shows the arrangement of the images in the three-dimensional matrix.

The arrangement of the images in this three-dimensional matrix here is the basis of the presentation of the images at a display in Step 26, which ensues using its arrangement of a three-dimensional matrix and the association of the dimensions with the spatial directions. In principle it can be said that a certain two-dimensional section from the matrix is always displayed on the presentation device 4, preferably in the sense of the comparative evaluation of multiple images. The arrangement of the images in the matrix is explained in detail in FIG. 4. The sorting criteria are shown again for clarification using icons 18, 20, 21 and 22. these icons can moreover also be displayed in the final presentation (discussed later), such that the evaluator is always aware of which sorting is present. The MR images are now shown in column 27, the CT images in column 28. The caudal images are arranged below, the cranial images above. The images are initially sorted chronologically going back (thus along the shown stack 29), in descending order according to T1-T2 weighting. The last sorting criterion is naturally omitted for CT images. Fewer images are also correspondingly indicated there in the stack 29. The matrix thus does not have to be completely populated in every dimension.

Figure 5:
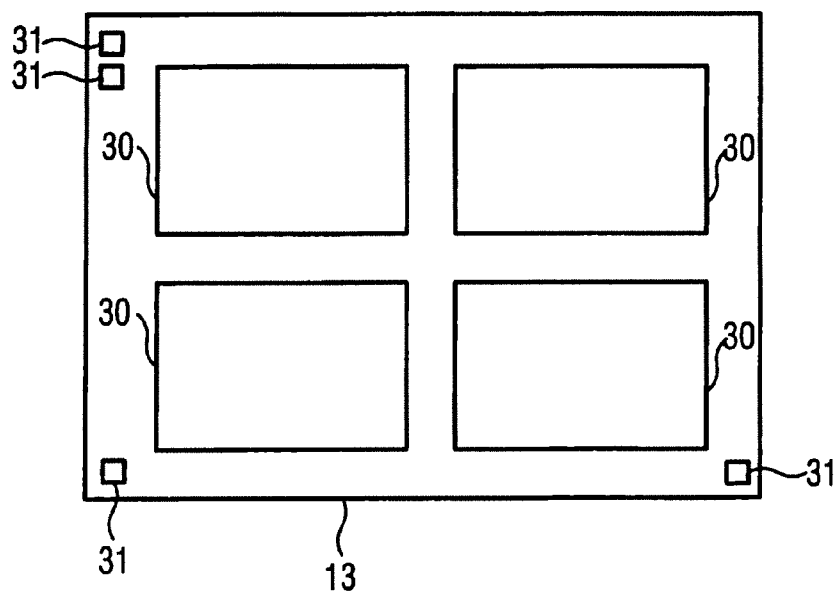
FIG. 5 shows a resulting presentation of the images of the image data sets via the user interface according to the invention.
Figure 6:
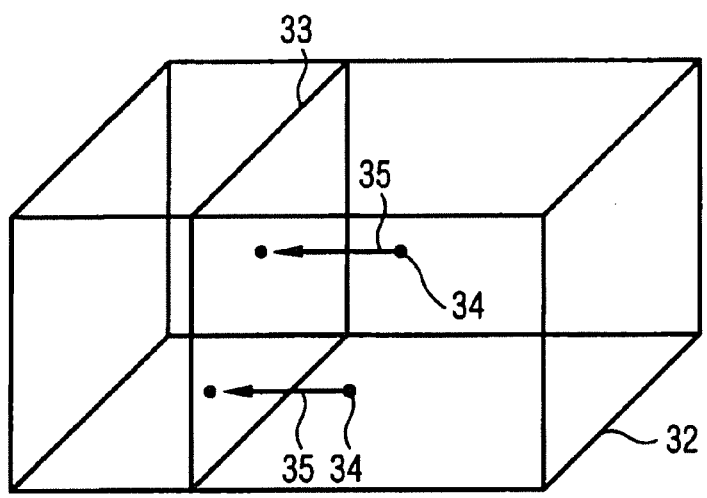
FIG. 6 shows a presentation to determine a projection of a three-dimensional image.
Figure 7:
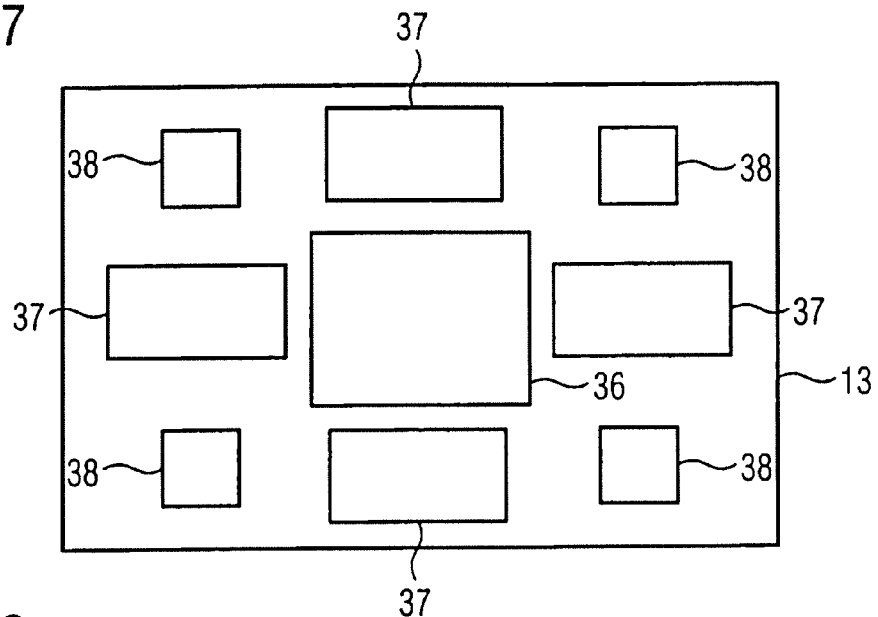
FIG. 7 shows an additional possibility to present the images.

Possibilities for presentation (Step 26 in FIG. 2) are now explained in detail with regard to FIG. 5-7.

FIG. 5 again shows the user interface 13 during Step 26, wherein a quite simple form of the presentation is selected. There four images 30 are respectively presented simultaneously. The evaluator can then comfortably compare these with one another. Icons 31 (here only schematically represented) indicate the organization parameters that are associated with the respective spatial directions.

In the method according to the invention and the user interface 13 according to the invention it is now also possible to consider various images or to modify the presentation with the use of input modalities 7-9 of the mouse 6. Namely, if the user moves the mouse 6 to the right, both of the images 30 to the left are masked out, and the following two images to the right of the right images 30 in the matrix are shown together with these. It behaves in the reverse when the mouse is moved to the left. A movement forward or back is intuitively, neatly associated with the spatial direction up-down in the presentation. Finally, the scroll wheel 9 is also used, namely in order to be able to navigate in the third dimension (thus with regard to the images situated before or, respectively, after the images 30) within the three-dimensional matrix. A very intuitive selection of the displayed images is possible in this way.

A zoom function is also additionally provided via which the number of the shown images (and correspondingly their presentation size) can be varied. A click on the left mouse button zooms in, thus reduces the number of the shown images—for example from four to two, then to one image. The one image then naturally takes up the entire available presentation space. A click on the right mouse button zooms out so that, for example, 9, 16 etc. images can be shown.

The presentations of images to be compared with one another can be adapted to one another within the scope of the method according to the invention. For example, the images 30 shown in FIG. 5 are all selected so that they show the exact same anatomical region. So that an association of the images of the image data sets with one another can also ensue, before the presentation the image data sets were registered with one another and/or corrected for distortion. The comparison is assisted in this manner. It is in particular also possible to simplify a comparison between three-dimensional and two-dimensional images. Namely, if a two-dimensional and a three-dimensional image follow one another in one spatial direction (as is shown in detail by FIG. 6), a projection is calculated from the three-dimensional image, which projection is then shown. Namely, if the three-dimensional image comprises the volume 32 in which the two-dimensional image 33 is situated in a specific orientation, the pixels of the three-dimensional image (of which here only two are shown for clarification) can projected onto the plan of the two-dimensional image 33 as indicated by the arrows 35. Naturally, other projection methods are also conceivable.

FIG. 7 shows an additional presentation form that can be used in Step 26 in the method according to the invention. There the size of the presented images varies. A centrally shown image 36 is largest; images 37 adjoining this are somewhat smaller, and outlying images 38 are smallest. The image situated in the middle is thus clearly emphasized. If the user now moves the mouse 6 to the right, for example, the right image 37 becomes the central image, correspondingly enlarged, while the previous central image 36 is reduced to the size of an image 37 etc. One image is thus always in focus, so to speak. Embodiments of the method according to the invention are also possible in which, for example, two central images are shown large.

Figure 8:
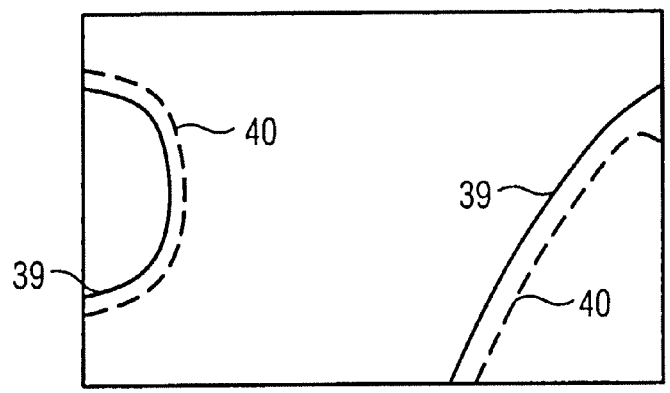
FIG. 8 shows the superimposed presentation of two images arranged in succession in the third dimension.

FIG. 8 now shows one possibility for superimposed presentation of two images 39, 40 that lie one behind the other in the third spatial direction. If it is also necessary to directly compare images situated one behind the other in the third spatial direction, such a configuration can be reasonable. Presently the image 40 situated in front (as is represented by the dashed lines) is shown transparent so that the image 39 behind it is visible. The image 39 is additionally shown in false colors in order to enable a further differentiation.

Figure 9:
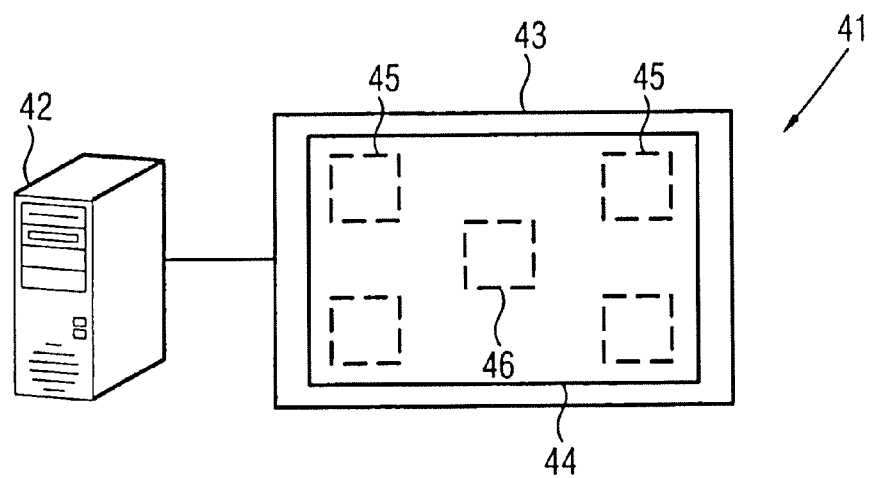
FIG. 9 shows an additional exemplary embodiment of a device according to the invention.

FIG. 9 shows a second exemplary embodiment of a device 41 according to the invention. This also comprises a computer 42 that ultimately can correspond to the computer 2. Here a two-dimensional device with a presentation surface 44 with quite a large area was selected as a presentation device 43 into which input means 45, 46 (here shown only schematically) that are fashioned as sensors are integrated. The input means 45 and 46 sense movements that occur above the presentation surface 44. The direction of these movements is thereby established, in particular those of a hand, wherein the input means 46 is a remote sensor. If a user now moves his or her hand parallel to the presentation surface 44 and over said presentation surface 44, in Step 26 of the method according to the invention, the user can scroll arbitrarily within the two-dimensional plane in which the user is currently located in the matrix, meaning that the user can page through the images. This procedure can also be continuous. If the user moves his or her hand away from the display surface 44 or toward the display surface 44, the third spatial direction is addressed; the user thus pages through the stack.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for presenting multiple image data sets in a display format allowing comparative evaluation of image content of the respective multiple image data sets, comprising:

in a processor, automatically determining at least three organization parameters that describe a sorting of images within an image data set, or image among a plurality of image data sets, each of said images having an image content comprising more information than is visually representable by an icon;

at a display in communication with said processor, visually displaying a display format comprising at least two displayed axes and comprising a plurality of said at least three organization parameters respectively as organization parameter icons;

via an input unit in communication with said processor, allowing manual interaction with said display format to selectively associate one of said organization parameter icons with one of said displayed axes;

in said processor, associating the organization parameter represented by said one of said organization parameter icons with at least one dimension of a three-dimensional matrix, said at least one dimension being associated with a spatial direction;

in said processor, arranging said image data sets at respective three-dimensionally defined positions in said three-dimensional matrix according to said at least three organization parameters and said at least one dimension; and from said processor, causing said image data sets to be visually displayed in said display format at said display according to said arrangement in said three-dimensional matrix and said at least one spatial dimension, with said image content of each of said displayed images being visible in said display format in a form allowing comparative evaluation the respective image content of the displayed images.

2. A method as claimed in claim 1 comprising allowing manual navigation within said three-dimensional matrix presented at said display by manipulating an input unit, in communication with said processor, having an input modality for spatial direction, respectively associated with the dimensions of said three-dimensional matrix, that are perpendicular to one another, selected from the group consisting of a zero-dimensional input modality and a one-dimensional input modality.

3. A method as claimed in claim 1 comprising allowing navigation within said three-dimensional matrix presented at said display by manipulating an input unit in communication with said processor having a two-dimensional input modality for two spatial directions respectively associated with dimensions of said three-dimensional matrix.

4. A method as claimed in claim 1 comprising navigating within said three-dimensional matrix presented at said display by manipulating an input unit in communication with said processor having a one-dimensional input modality allowing interactive actuation along said spatial direction associated with said at least one dimension.

5. A method as claimed in claim 1 comprising presenting said images at said display in a two-dimensional presentation having two spatial directions associated therewith, and allowing selection of individual ones of the images in said three-dimensional matrix in a third direction by operating a computer mouse in communication with said processor, by an operation selected from the group consisting of combined actuation of two actuation directions of said computer mouse that are perpendicular to each other by moving said mouse on a pad, and operating a scroll wheel of said computer mouse.

6. A method as claimed in claim 1 comprising varying a number of said images presented at said display and a corresponding variation of a size of the presented images by selecting a zoom function.

7. A method as claimed in claim 6 comprising navigating among said images presented in said three-dimensional matrix at said display with a first input modality, and selecting said zoom function with a second input modality.

8. A method as claimed in claim 1 comprising presenting said images at said display with respectively different presentation sizes with a central one of the displayed images having a larger size than images presented at an edge of display.

9. A method as claimed in claim 1 comprising presenting said images in a two-dimensional presentation at said display and, in said presentation, overlapping a currently presented image with a following or preceding image in a third dimension of said three-dimensional matrix, using a presentation effect selected from the group consisting of a transparency effect and a false color effect.

10. A method as claimed in claim 1 comprising allowing selection of said image data to be presented at said display by user-operated manipulation of said input unit in communication with said processor.

11. A method as claimed in claim 1 comprising, in said processor, automatically determining at least a portion of said organization parameters from at least one of said image data sets.

12. A method as claimed in claim 11 comprising storing said organization parameters in said at least one image data set.

13. A method as claimed in claim 11 comprising determining said at least one organization parameter by backward calculation from image data of said at least one image data set.

14. A method as claimed in claim 1 comprising allowing selection of said organization parameters and said at least one dimension by user manipulation of said input unit connected to said processor.

15. A method as claimed in claim 1 comprising associating more than one of said organization parameters with one of said dimensions.

16. A method as claimed in claim 15 comprising, in said processor, sorting said images in said one dimension having more than one organization parameter associated therewith in an order determined by association of said organization parameters with said one dimension.

17. A method as claimed in claim 1 comprising, in said processor employing organization parameters selected from the group consisting of an acquisition time of said image data sets, a time of administration of a contrast agent to generate said image data sets, spatial dimensions within an image data set, at least one image acquisition parameter used to acquire the image data sets, a magnetic resonance sequence used to acquire said imaged data sets, an evaluation parameter for evaluating said image data sets, a filter type for evaluating said image data sets, an orientation of said image data sets in a patient, and an imaging modality used to acquire said imaged data sets.

18. A method as claimed in claim 1 comprising, before presenting said image data sets at said display, editing said image data sets to be displayed, in said processor, by an editing function selected from the group consisting of bringing said image data sets into registration with each other, and correcting for distortion in said image data sets.

19. A method as claimed in claim 1 comprising presenting successive images in one dimension of said three-dimensional matrix at said display with identical presentation parameters to facilitate said comparative evaluation among said images presented at said display.

20. A method as claimed in claim 1 wherein said images are two-dimensional images and three-dimensional images and comprising, in said processor, determining, for each of said three-dimensional images that is displayed, a two-dimensional projection thereof that corresponds to a projection of the two-dimensional images that are displayed, and presenting said three-dimensional images at said display with said two-dimensional projection.

21. A method as claimed in claim 1 comprising, in said processor, adapting successive images presented in said display with each other with regard to an anatomical region shown therein.

22. A user interface for presenting multiple image data sets in a display format allowing comparative evaluation of image content of the respective multiple image data sets, comprising:
- a processor configured to automatically determine at least three organization parameters that describe a sorting of images within an image data set, or image among a plurality of image data sets, each of said images having an image content comprising more information than is visually representable by an icon;
- a display in communication with said processor, said processor being configured to visually display a display format at said display comprising at least two displayed axes and comprising a plurality of said at least three organization parameters respectively as organization parameter icons;
- an input unit in communication with said processor being configured to allow manual interaction with said display format to selectively associate one of said organization parameter icons with one of said displayed axes;
- said processor being configured to associate the organization parameter represented by said one of said organization parameter icons with at least one dimension of a three-dimensional matrix, said at least one dimension being associated with a spatial direction;
- said processor being configured to arrange said image data sets at respective three-dimensionally defined positions in said three-dimensional matrix according to said at least three organization parameters and said at least one dimension; and
- said processor being configured to cause said image data sets to be visually displayed in said display format at said display according to said arrangement in said three-dimensional matrix and said at least one spatial dimension, with said image content of each of said displayed images being visible in said display format in a form allowing comparative evaluation the respective image content of the displayed images.

23. A user interface as claimed in claim 22 wherein said input unit is configured to implement a first input modality wherein said input unit is manipulatable to allow manual navigation among said images presented in said three-dimensional matrix at said display, and to implement a second input modality to select a zoom function.

24. A user interface as claimed in claim 22 wherein said processor is configured to present said images at said display with respectively different presentation sizes with a central one of the displayed images having a larger size than images presented at an edge of display.

25. A user interface as claimed in claim 22 wherein said processor is configured to present said images in said two-dimensional presentation at said display by overlapping a currently presented image with a following or preceding image in a third dimension of said three-dimensional matrix, using a presentation effect selected from the group consisting of a transparency effect and a false color effect.

26. A user interface as claimed in claim 22 wherein said processor is configured to present successive images in one dimension of said three-dimensional matrix at said display with identical presentation parameters to facilitate said comparative evaluation among said images presented at said display.

27. A user interface as claimed in claim 22 wherein said images are two-dimensional images and three-dimensional images and wherein said processor is configured to determine, for each of said three-dimensional images that is displayed, a two-dimensional projection thereof that corresponds to a projection of the two-dimensional images that are displayed, and to present said three-dimensional images at said display with said two-dimensional projection.

28. A user interface as claimed in claim 22 wherein said processor is configured to adapt successive images presented in said display with each other with regard to an anatomical region shown therein.

* * * * *